United States Patent [19]
Pagan

[11] Patent Number: 5,746,202
[45] Date of Patent: May 5, 1998

[54] INTRODUCER FOR ORAL TUBES

[75] Inventor: Eric Pagan, Folkestone, England

[73] Assignee: Smiths Industries PLC, London, England

[21] Appl. No.: 672,070

[22] Filed: Jun. 26, 1996

[30] Foreign Application Priority Data

Jul. 7, 1995 [GB] United Kingdom .................. 9513860

[51] Int. Cl.$^6$ .......................... A61M 16/00; A62B 9/02; A62B 9/06
[52] U.S. Cl. .................. 128/207.14; 128/207.15; 128/200.26; 128/DIG. 26; 128/912
[58] Field of Search .................. 128/200.26, 207.14, 128/207.15, 207.17, 911, 912, DIG. 26

[56] References Cited

U.S. PATENT DOCUMENTS

| | | | |
|---|---|---|---|
| 2,693,182 | 11/1954 | Phillips | 128/200.26 |
| 2,756,742 | 7/1956 | Barton | 128/200.26 |
| 4,198,970 | 4/1980 | Luomanen | 128/200.26 |
| 4,351,331 | 9/1982 | Gereg . | |
| 4,683,882 | 8/1987 | Laird . | |
| 4,774,944 | 10/1988 | Mischinski . | |
| 5,024,218 | 6/1991 | Ovassapian et al. | 128/200.26 |
| 5,069,206 | 12/1991 | Crosbie . | |
| 5,295,480 | 3/1994 | Zemo . | |

FOREIGN PATENT DOCUMENTS

| | | |
|---|---|---|
| 2111394 | 7/1983 | United Kingdom . |
| 2259454 | 3/1993 | United Kingdom . |
| 2298796 | 9/1996 | United Kingdom . |

*Primary Examiner*—Kimberly L. Asher
*Attorney, Agent, or Firm*—Pollock, Vande Sande & Priddy

[57] ABSTRACT

A securing device for an introducer of the kind for introducing an oral tube or laryngeal mask into a patient takes the form of a V-shape plate with a ribbed collar at its apex within which the tube or mask extends. A compressible gap extends from the collar to the edge of the plate and this is compressed, so that the collar grips the tube or mask, by fastening openings in the plate onto projections from the introducer. Alternatively, the securing device has a clip with two spaced engagement members so that the gap is squeezed closed by clipping the engagement members between two arms of the introducer.

16 Claims, 4 Drawing Sheets

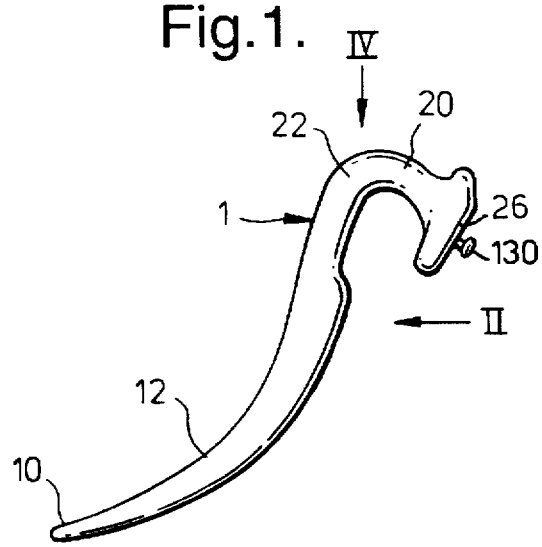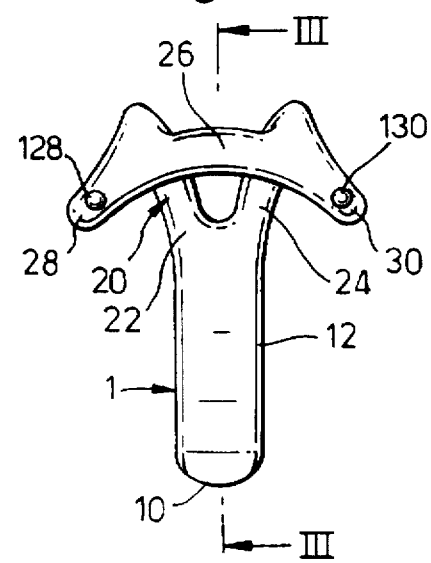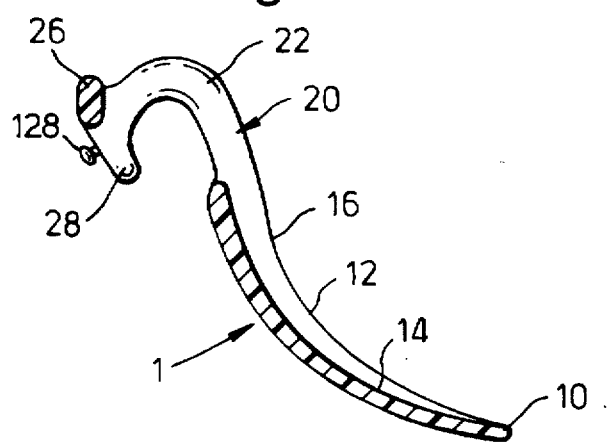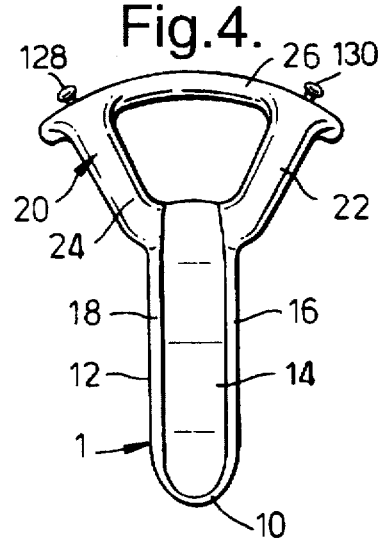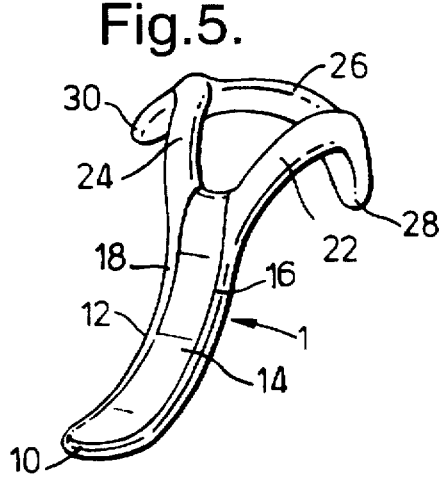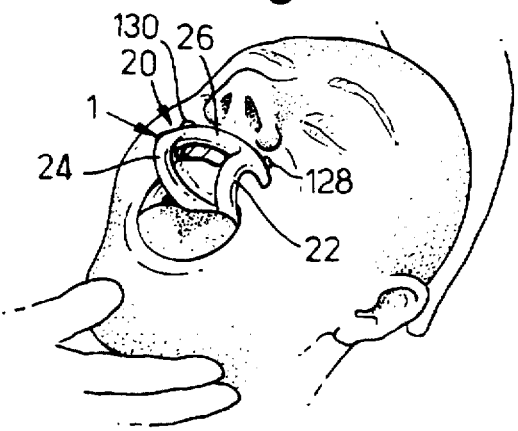

INTRODUCER FOR ORAL TUBES

BACKGROUND OF THE INVENTION

This invention relates to securing devices for medico-surgical introducers and to assemblies including an introducer and securing device.

It is common practice to use an airway known as a laryngeal mask for the administration of anaesthetic and ventilation gases to a patient. These airways comprise a tube with a mask or cuff at one end, the tube being inserted in the patient's mouth so that one end is located in the hypopharynx and so that the mask forms a seal in this region with the surrounding tissue. Laryngeal masks have several advantages over endotracheal tubes, which are longer and seal with the trachea below the vocal folds. When laryngeal masks are inserted, however, they can cause trauma to the pharyngeal wall. In GB 2259454 and 9603045 there are described introducers for a laryngeal mask, which can be used to facilitate insertion and reduce the risk of injury to the patient. Another problem with laryngeal masks and other tubes is that they can be displaced longitudinally or about their axis, such as by moving tubing connected to the mask or tube, or if the patient's head is moved during surgery. This is a problem because it can cause damage to tissue contacted by the mask or tube, or it may compromise the seal of the sealing cuff with the patient.

BRIEF SUMMARY OF THE INVENTION

It is an object of the present invention to provide a device that enables improved securing of a laryngeal mask or tube.

According to one aspect of the present invention there is provided a securing device for use with an introducer of the kind for introducing an oral tube or laryngeal mask into a patient, the securing device having an engagement member arranged to engage the introducer, an opening arranged to receive the oral tube or laryngeal mask as a close fit, and a region of variable width between the opening and an edge of the securing device, and the securing device being shaped such that when its engagement member is engaged with the introducer the region of variable width is retained with a narrow width so that the securing device is clamped about the oral tube or laryngeal mask The region of narrow width is preferably a gap extending between the opening and the edge of the securing device and the securing device may have two engagement members arranged to engage different parts of the introducer. The or each engagement member is preferably an opening adapted to receive a projection on the introducer. The securing device preferably has a projecting collar arranged to embrace the oral tube or laryngeal mask, the collar having ribs on its inner surface to enhance the grip on the tube or mask.

The securing device may be a planar device of V-shape having two arms inclined away from one another, the region of variable width being formed between the two arms.

Alternatively, the securing device may have a clip arranged to engage between two arms of the introducer. The device may have two bite guards arranged to project forwardly alongside the oral tube or laryngeal mask, and two finger grips located on opposite sides of the region of variable width to facilitate positioning the device on the oral tube or laryngeal mask.

According, to another aspect of the present invention there is provided an assembly of a securing, device according to the above one aspect of the invention and an introducer for introducing an oral tube or laryngeal mask.

According to a further aspect of the present invention there is provided an assembly of a securing device according to the above one aspect of the invention, an introducer and an oral tube or laryngeal mask.

An introducer assembly with a laryngeal mask and a securing device, according to the present invention, will now be described by way of example, with reference to the accompanying drawings.

BRIEF DESCRIPTION OF THE DRAWINGS

FIG. 1 is a side elevation view of the introducer;

FIG. 2 is a side elevation view of the introducer along the arrow II in FIG. 1;

FIG. 3 is a cross-sectional side elevation view along the line III—III of FIG. 2;

FIG. 4 is a side elevation view of the introducer along the arrow IV in FIG. 1;

FIG. 5 is a perspective view of the introducer;

FIGS. 6 to 8 illustrate steps in use of the introducer;

DETAILED DESCRIPTION OF THE PREFERRED EMBODIMENTS

Figure 7:
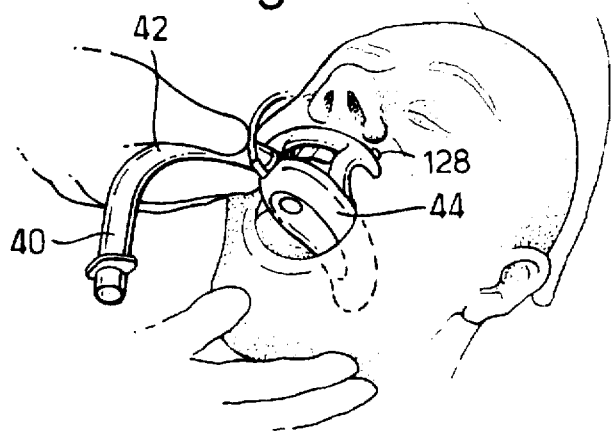

With reference to FIGS. 1 to 5, the introducer device 1 is about 100 mm long and is moulded from a soft plastics material, such as PVC, or a natural or synthetic rubber. The introducer device can be moulded as a single, integral moulding or made from separate parts moulded together. Alternatively, different parts of the device could be made separately and subsequently clipped or joined together is some other way. The patient end or forward tip 10 of the introducer is rounded and is about 18 mm wide. A channel-shape portion 12 extends rearwardly from the tip along the major part of the length of the introducer and is curved with a radius of curvature of about 58 mm, the channel being open on the inside of the curve. The channel portion 12 has a flat floor 14 across its width and has two shallow walls 16 and 18 along opposite edges, which project from the concave side and increase in height from the patient end 10 to be about 8 mm high at the rear, or machine, end of the portion. The channel-shape portion 12 is about 80 mm long and joins at its machine end with a bite block region 20.

The bite block region 20 is formed by bifurcating, or dividing the device into two arms 22 and 24 at the machine end of the channel portion 12. The arms 22 and 24 are thickened and are of substantially circular section, being about 8 mm in diameter. The arms 22 and 24 incline away from one another at an angle of about 50° and initially extend in a flat plane being a continuation of the plane including the machine end of the channel portion 12. After about 20 mm, the two arms 22 and 24 curve in the opposite direction from the channel portion 12 through a relatively tight curve with a radius of about 8 mm and continue for a distance of about 15 mm. At their machine end, the arms 22 and 24 are joined by a laterally-extending bridge piece 26, which is about 10 mm wide and about 5 mm thick. The bridge piece 26 is curved along its length with a center of curvature coincident with the intersection of the axes of the two arms 22 and 24. The bridge piece 26 is also curved along its length in a plane including the width of the bridge piece so that opposite ends of the bridge piece extend downwardly. The bridge piece is extended at its ends beyond the arms to a width of about 62 mm to form two bollards 28 and 30 with smoothly rounded ends. Two short pegs 128 and 130 project on the upper surface of the bollards 28 and 30 respectively.

The dimensions and shape of the introducer 1 are selected to conform to the anatomy of the patient so that the channel portion 12 extends along the hard palate with the tip 10 being located in the pharynx. In this position, the two arms 22 and 24 project between the teeth of the patient and curve cephaladly over the upper lip, with the bridge piece 26 extending along the skin between the nose and the mouth.

The introducer 1 is used by first placing the patient in the usual position for introduction of an oral tube or laryngeal mask, with his neck flexed, his head rotated back and his mouth open, as shown in FIG. 6. The introducer 1 is lubricated over the channel portion 12 on both sides, such as with a hydrophilic gel, and is gripped by the bite block region 20 with the tip 10 pointing down the patient's mouth and with the open side of the channel 12 directed caudally. The forward end of the introducer 1 is pushed into the patient's mouth so that the convex side of the channel portion 12 slides smoothly over the hard palate and pharynx until the arms 22 and 24 extend between the teeth, with the bridge piece 26 lying against the skin just above the upper lip. In this position the tip 10 of the introducer lies in the region of the pharynx. The introducer 1 is relatively flexible at its patient end, because of the low height of the side walls 16 and 18 at the patient end 10, so that it readily conforms to the patient's anatomy as it is slid into position, without trauma. Damage to the patient's teeth during insertion is also avoided because of the flexible nature of the introducer. When correctly located, the introducer provides a guide along which an airway can be inserted.

Figure 8:
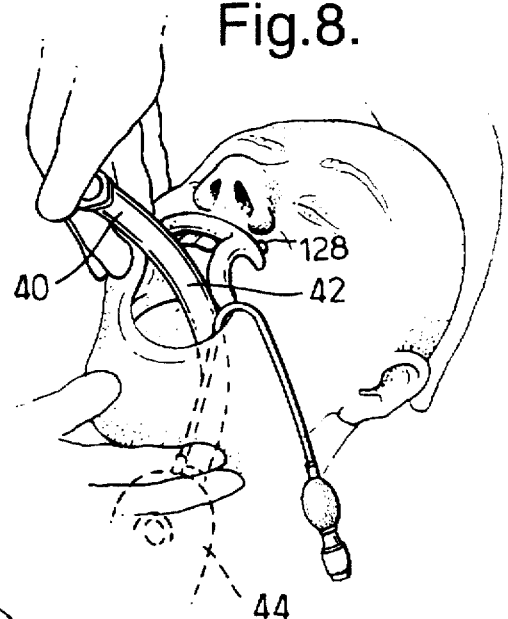

As shown in FIGS. 7 to 8, the airway 40 is a laryngeal mask of conventional form, such as described in GB 2111394, and comprises a curved tube 42 opening at one end into a cuff or hollow mask 44 located on one side of the tube. In use, the mask 44 conforms to the space behind the larynx and seals around the circumference of the laryngeal inlet but without penetrating the larynx itself. The airway 40 is inserted in the manner shown in FIG. 7, by directing the open side of the mask 44 away from the introducer and resting it on the two arms 22 and 24, with the tip of the mask contacting the machine end of the channel portion 12 of the introducer just inside the patient's mouth. The gap between the two arms 22 and 24 is not sufficient to receive the mask 44, while the width of the channel portion 12 of the introducer 1 is such that the tubular component 42 of the airway is received snugly within it, with the mask overlapping the edges of the channel on both sides. The airway 40 is then slid along the introducer, in the manner shown in FIG. 8, which guides it to the position shown in FIG. 9. Because the introducer 1 is located between the airway 40 and the patient's tissue, it protects the pharynx and hard palate from the airway, thereby reducing trauma. The flexible nature of the introducer enables it to mould itself to the shape of the palate and pharynx as the mask is inserted, thereby reducing localized pressure on the patient's tissue.

The thickness of the arms 22 and 24 where they project between the teeth is sufficient to act as a bite block on either side of the tubular part 42 of the airway 40. In this respect, the thickness of the arms 22 and 24 is preferably at least equal to the diameter of the tubular part of the airway but it will be appreciated that sufficient protection may be afforded to the airway if the arms are slightly thinner than the airway because, although the teeth may contact the airway they would not be able to compress the airway sufficiently to occlude or damage it. The bridge piece 26 limits the extent of insertion of the introducer 1 and thereby prevents the patient swallowing the device.

Figure 9:
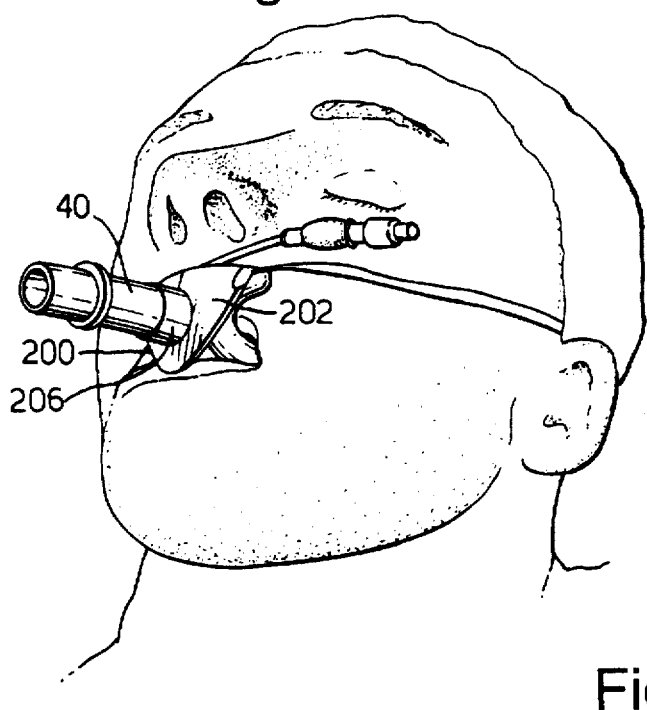
FIG. 9 is a perspective view showing the assembly of the introducer and securing device in use.
Figure 10:
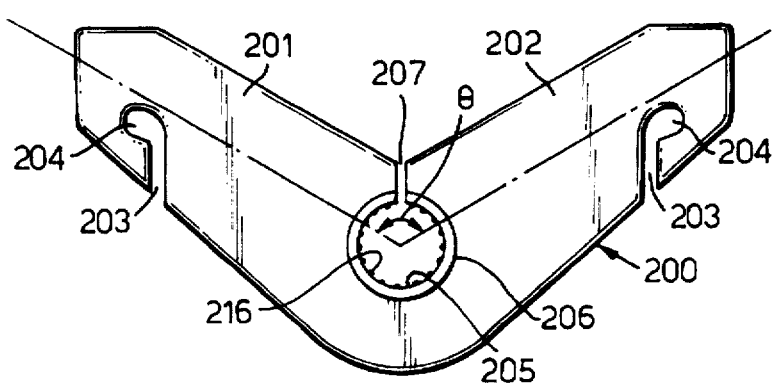
FIG. 10 is a plan view of the securing device.

The introducer assembly also includes a planar securing device in the form of an anti-rotation plate 200, of the kind shown in FIGS. 9 and 10. The plate 200 is a one-piece, integral moulding of a stiff, resilient plastics material, such as nylon, and is about 2 mm thick. The plate 200 is of V-shape with two arms 201 and 202 inclined to one another at an angle θ of 110°. Each arm 201 and 202 has a vertical slot 203 with an enlarged inner end 204 formed in the lower edge of the arm, towards its end. These slots 203 are shaped to receive the projecting pegs 128 and 130. A circular opening 205 is formed through the plate 200 in the apex between the two arms 201 and 202. In its natural state, before assembly of the plate 200 on the introducer 1, the diameter of the opening 205 is 14 mm, that is, slightly smaller than the external diameter of the airway tube 40 with which the introducer is to be used. Surrounding the opening 205 is a collar 206, about 10 mm high, formed integrally of the plate and projecting away from the patient. The interior surface of the collar 206 has axial ribs 216 to improve the grip on the airway 40. A narrow compressible region of variable width in the form of a gap 207 extends through the upper edge of the plate into the opening 205 and along the length of the collar 206. This gap 207 enables the two arms 201 and 202 to be flexed away from one another in the plane of the plate 200, to increase the angle θ and thereby increase the diameter of the opening 205 and the collar 206.

The plate 200 is assembled on the introducer 1 after the laryngeal airway is in position. The machine end of the airway is aligned with the opening 205 and the two arms 201 and 202 are pulled apart slightly to enlarge the opening and the collar 206 sufficiently for the airway 40 to enter. The plate 200 is pushed forwardly until it contacts the machine end of the introducer 1. The arms 201 and 202 are then squeezed together so that the slots 203 can be pushed onto the pegs 128 and 130. The engagement of the pegs 128 and 130 in the slots 203 holds the arms 201 and 202 together, it retains the narrow width of the gap 207 and compresses the collar 206 tightly around the airway. This effectively grips the airway 40 and stabilizes it, preventing it from being displaced rotationally or along its length relative to the introducer.

The plate 200 need not be slipped onto the airway from its end, since this may not be convenient if the machine end of the airway is already connected to a coupling or other component. Instead, the plate 200 can be pushed onto the airway from the side, access to the opening 205 being via the gap 207.

In an alternative plate, the compressible region is provided by a region of a different, or thinner material, that can be compressed, to enable the two arms of the plate to be squeezed together. In such an alternative arrangement, the introducer would have to be slipped onto the tube from its machine end, instead of from the side.

Figure 11:
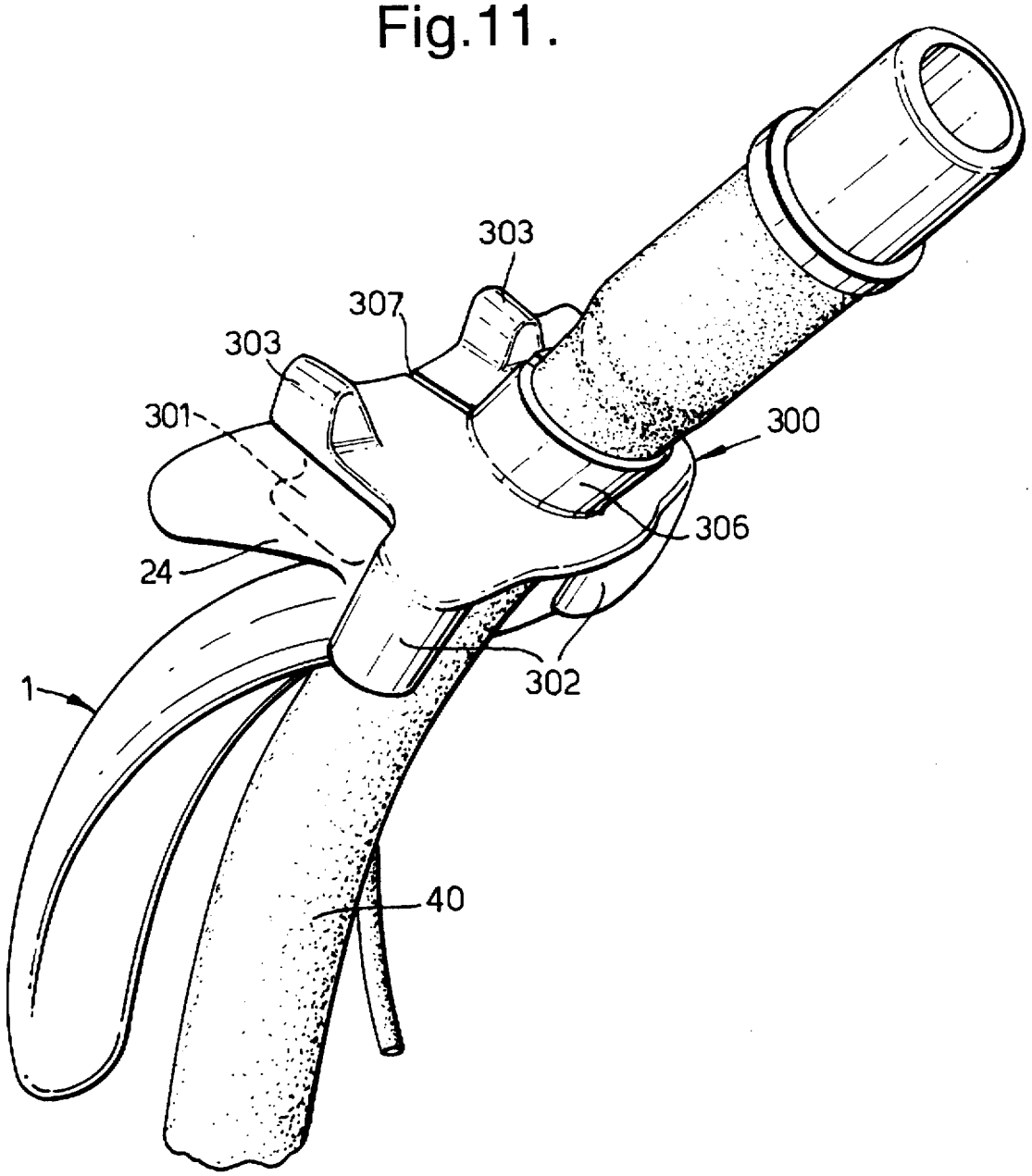
FIG. 11 is a perspective view of an alternative securing device.
Figure 12:
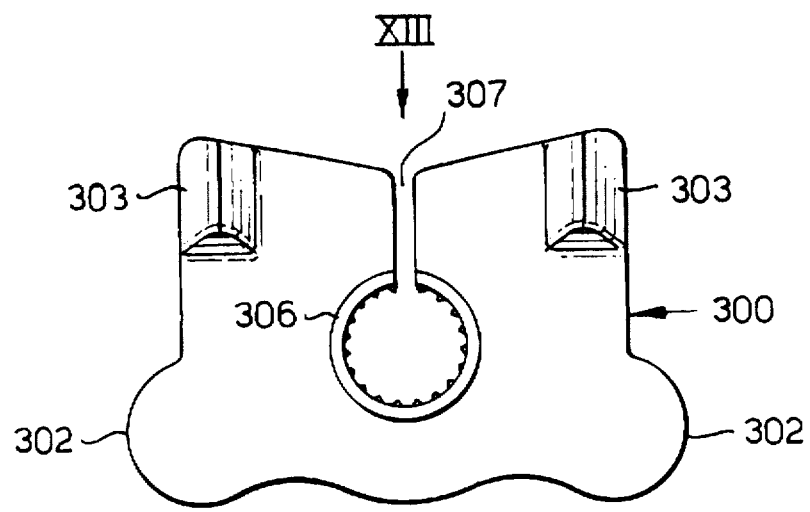
"FIG. 12 is a plan view of the securing device of FIG. 11.
Figure 13:
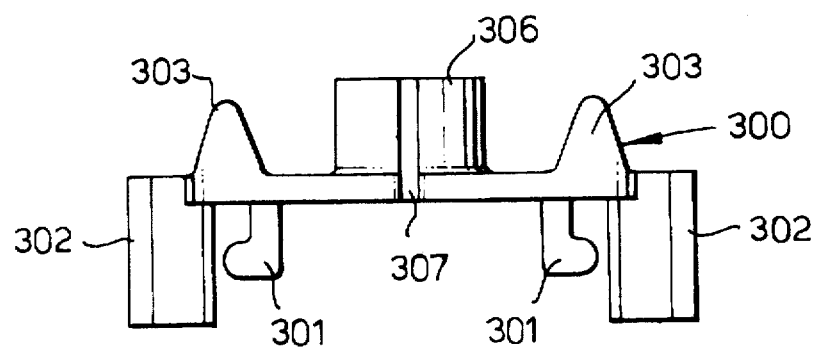
" "FIG. 13 is a side elevation view along the arrow XIII in FIG. 12".

The securing device could be retained with the introducer by means other than the engaging projections and openings of the kind described above. In the arrangement shown in FIG. 11, there is shown an alternative securing device 300 in the form of a moulded body having a clip 301 projecting from a forward face of a planar region of the device. The clip 301 extends between and clips onto the two arms 22 and 24 of the introducer 1 so as to engage the introducer and prevent rotation of the securing device 300 relative to the introducer. The clip 301 comprises two engagement members, one on either side of the gap 307, so that the gap is compressed to a narrow width when the clip is engaged. The securing device 300 also has two bite guards 302 projecting from its forward face and extending alongside the airway 40 on the side opposite from the introducer 1. These bite guards 302 give the airway 40 additional protection from damage by the patient's teeth. Two finger grips 303 project from the rear surface of the securing device 300 on opposite sides of the gap 307. The finger grips 303 are used to open the gap for introduction of the airway 40 and facilitate general positioning of the securing device 300.

What I claim is:

1. A securing device in combination with an introducer of the kind adapted for introducing an oral tube into a patient, wherein the securing device comprises: engagement members shaped to engage said introducer; an opening in said securing device having a shape adapted to receive an oral tube in a close fit; and a region of variable width in said securing device between said opening and an edge of said securing device such that when said engagement member is engaged with said introducer said region of variable width is compressed and the securing device will be clamped about said oral tube.

2. A securing device according to claim 1, wherein said region of variable width is a gap extending between said opening and said edge of the securing device.

3. A securing device according to claim 1 or 2, wherein said engagement members are arranged to engage different parts of said introducer.

4. A securing device according to claim 1, wherein said introducer has projections thereon and said engagement members are openings for receiving said projections on said introducer.

5. A securing device according to claim 1, wherein the securing device opening has a projecting collar having a shape adapted to embrace the oral tube, and wherein said collar has ribs on an inner surface to enhance the grip on an oral tube.

6. A securing device according to claim 1, wherein the securing device is a planar device of V-shape having two arms inclined away from one another, and wherein said compressible region is formed between said two arms.

7. A securing device according to claim 1, wherein said introducer has two arms and said engagement members of the securing device comprise a clip arranged to engage said two arms of said introduce between said two arms.

8. A securing device according to claim 7, wherein the securing device has two bite guards arranged to project forwardly alongside an oral tube engaged by said securing device.

9. A securing device according to claim 7 or 8, wherein the securing device has two finger grips located on opposite sides of said region of variable width, and wherein said finger grips facilitate positioning the securing device an oral tube.

10. A securing device in combination with an introducer of the kind adapted for introducing an oral tube into a patient, wherein the securing device comprises: a planar member, two engagement members on said planar member, said engagement members being shaped to engage different parts of said introducer; an opening in said securing device having a shape adapted to receive an oral tube with a close fit; and a gap extending between said opening and an edge of said securing device such that when said engagement members are engaged with said introducer said gap is retained narrow and the securing device clamps about an oral tube.

11. A securing device in combination with an introducer of the kind adapted for introducing an oral tube into a patient, wherein the securing device comprises: a moulded body; a clip projecting from one side of the body, said clip having two engagement members shaped to engage two arms on said introducer; an opening in said body shaped to receive an oral tube with a close fit; and a gap extending in a region between said two engagement members between said opening and an edge of said securing device such that when said engagement members are engaged with said arms of said introducer said gap is retained narrow and the securing device clamps about an oral tube.

12. The securing device of one of claims 1, 10 or 11 wherein the introducer is of the kind adapted for introducing an oral tube having a laryngeal mask at its patient end.

13. An assembly comprising: an introducer; an oral tube on said introducer; and a securing device, wherein said securing device includes engagement members, said engagement members being engaged with said introducer, an opening in said securing device within which said oral tube extends with a close fit, and a region of variable width in said securing device between said opening and an edge of said securing device, said region of variable width being retained narrow by engagement of the engagement members with the introducer so that the securing device is clamped about said oral tube.

14. An assembly comprising: an introducer; an oral tube on said introducer; and a securing device, wherein the securing device comprises: a planar member; two engagement members on said planar member, said engagement members engaging different parts of said introducer; an opening in said securing device within which said oral tube extends with a close fit; and a gap extending between said opening and an edge of said securing device, said gap being retained narrow by engagement of said engagement members on said introducer so that the securing device is clamped about said oral tube.

15. An assembly comprising: an introducer; an oral tube on said introducer; and a securing device, wherein the securing device comprises: a moulded body; a clip projecting from one side of said body, said clip having two engagement members engaging two arms on said introducer; an opening in said body within which said oral tube extends as a close fit; and a gap extending in a region between said two engagement members between said opening and an edge of said securing device such that said gap is retained narrow by engagement of said engagement members on said arms of said introducer so that the securing device is clamped about said oral tube.

16. The assembly of one of claims 13, 14 or 15 wherein said oral tube has a laryngeal mask at its patient end, said laryngeal mask having a shape adapted to form a seal in the region of the hypopharynx.

* * * * *